United States Patent [19]

Barry et al.

[11] 4,377,692

[45] Mar. 22, 1983

[54] ANOMALOUS SALTS OF DIBASIC ACIDS

[75] Inventors: John E. Barry, Adams; Manuel Finkelstein, North Adams; Sidney D. Ross, Williamstown, all of Mass.

[73] Assignee: Sprague Electric Company, North Adams, Mass.

[21] Appl. No.: 286,436

[22] Filed: Jul. 24, 1981

[51] Int. Cl.$^3$ .......................................... C07D 295/04
[52] U.S. Cl. .................................... 546/186; 546/189; 546/184; 260/501.1; 260/501.15; 252/62.2
[58] Field of Search ...................... 260/501.1, 501.15; 546/184, 186, 189

[56] References Cited

U.S. PATENT DOCUMENTS 3,909,682  9/1975  Dunkl et al. ...................... 260/501.1

FOREIGN PATENT DOCUMENTS 2048262  12/1980  United Kingdom ............. 260/501.1

OTHER PUBLICATIONS

Speakman, J. C., 'Acid Salts of Carboxylic Acids, Crystals with some "Very Short" Hydrogen Bonds' Structure and Bonding 12: 141–199, (1972).

Primary Examiner—Robert T. Bond

[57] ABSTRACT

Anomalous substituted-amine or quaternary ammonium salts of dibasic acids have two dibasic acid molecules per cation of three per two cations.

10 Claims, No Drawings

ANOMALOUS SALTS OF DIBASIC ACIDS

BACKGROUND OF THE INVENTION

The present invention relates to new chemical compounds and more particularly to anomalous substituted-amine or quaternary ammonium salts of dibasic acids in which there are two dibasic acid molecules per cation or three dibasic acid molecules per two cations. The salts have the general formulae $RH_3Y_2$ and $R_2H_4Y_3$ in which $H_2Y$ is the dibasic acid and R is the cation.

Salts of the first group that have been reported are a potassium acid succinate, $KH_3Y_2$, a potassium acid glutarate, $KH_3Y_2$, and acid oxalates, $MH_3Y_2$, in which the cation is potassium, rubidium, thallium, or ammonium. Salts of the second type are rare, but a sodium cyclobutane-trans-1,3-dicarboxylate, $Na_2H_4Y_3$, is known.

Monosalts of dibasic acids are of interest as solutes in organic electrolyte systems, particularly for electrolytic capacitors. It was while attempting to prepare these monosalts that the anomalous salts of the present invention were discovered. These salts dissociate in solution and are useful as electrolyte solutes, particularly where a slightly acidic electrolyte is desired. They may also find utility as buffers of known composition.

SUMMARY OF THE INVENTION

Anomalous substituted-amine or quaternary ammonium salts of dibasic acids have two acid groups per cation or three acid groups per two cations. They may be represented by $RH_3Y_2$ or $R_2H_4Y_3$ in which $H_2Y$ is the dibasic acid and R is the cation grouping. In the first group, $RH_3Y_2$, two dibasic acid groups are joined together, probably by hydrogen bonds, and only one of the four carboxyl groups is neutralized. In the second group, $R_2H_4Y_3$, three dibasic acid groups are joined, again probably by hydrogen bonds, and four carboxyl groups are unneutralized.

The anomalous salts were obtained while trying to prepare the normal acid salts. When attempting to prepare other anomalous salts for study, the normal salts were generally obtained. The anomalous salts occurred most frequently when the base was a quaternary ammonium hydroxide, but the result in any particular case was unpredictable.

DESCRIPTION OF THE PREFERRED EMBODIMENTS

The acids that formed anomalous salts were butanedioic (succinic), pentanedioic (glutaric), hexanedioic (adipic), cis-butenedioic (maleic), trans-butenedioic (fumaric), and ortho-phthalic acids. The bases that gave these salts were tetramethylammonium hydroxide, tetraethylammonium hydroxide, tert-butylamine, tri-n-propylamine, and N-ethylpiperidine, but not all bases formed anomalous salts with all acids.

Thus, fumaric acid would only form an anomalous salt $RH_3Y_2$ with tetramethylammonium hydroxide at acid:base ratios of 1:1, 3:2, or 2:1. With tetraethylammonium hydroxide, the anomalous salt $R_2H_4Y_3$ was obtained at acid:base ratios of 2:1 or 3:1. When this salt was crystallized from 2-propanol, it was converted to the normal monosalt. With tert-butylamine, the anomalous salt $R_2H_4Y_3$ was obtained at acid:base ratios of 1:1 or 3:2, but the normal disalt was obtained at a 1:2 ratio. With piperidine, only the normal monosalt was obtained at 1:1 and 2:1 acid:base ratios.

With maleic acid and tetramethylammonium hydroxide, a normal salt was obtained at a 1:1 acid:base ratio but an anomalous salt $RH_3Y_2$ at a 2:1 ratio. With tert-butylamine, only normal salts were obtained.

Phthalic acid and tetramethylammonium hydroxide or tetraethylammonium hydroxide gave the anomalous salt $RH_3Y_2$ at an acid:base ratio of 2:1. These salts could be recrystallized from 2-propanol without change in composition. However the normal monosalt was obtained at a 1:1 ratio using tetramethylammonium hydroxide and by crystallization from methanol. Only normal salts were obtained with tert.butylamine.

Glutaric acid and tri-n-propylamine gave the anomalous salt $RH_3Y_2$ at an acid:base ratio of 1:1, 3:2, and 2:1, while adipic acid and tri-n-propylamine gave the anomalous salt $R_2H_4Y_3$ at an acid:base ratio of 1.2:1, 1:1, and 3:2. Succinic acid forms an anomalous salt $R_2H_4Y_3$ with N-ethylpiperidine at an acid:base ratio of 1:1 and 3:2.

Table 1 gives the melting points, the analyses of the anomalous salts prepared, and pH in water (if sufficiently soluble) or water-glycol mixtures; the concentration was 0.1 M in water and 0.05 M in 50% water-50% glycol. The first five have the general formula $RH_3Y_2$ and the last four, $R_2H_4Y_3$. NE stands for neutral equivalent. The salts are named similarly to the more common anomalous acid salts of monocarboxylic acids, e.g. $NaH(HCO_2)_2$ has the general formula $MHY_2$, where HY is the acid and M is the metallic cation, and is named sodium hydrogen di-formate. In like manner, the anomalous salt of fumaric acid with tetramethylammonium hydroxide of general formula $RH_3Y_2$, described above, is tetramethylammonium tri-hydrogen di-fumarate and the anomalous salt with tetraethylammonium hydroxide of general formula $R_2H_4Y_3$ is di-(tetraethylammonium) tetrahydrogen tri-fumarate.

TABLE 1

| Salt | mp, °C. | Calcd C | Calcd H | Calcd N | Calcd NE | Found C | Found H | Found N | Found NE | pH $H_2O$ | pH $H_2O$-glycol |
|---|---|---|---|---|---|---|---|---|---|---|---|
| Tetramethylammonium trihydrogen di-fumarate | 199d | 47.21 | 6.27 | 4.59 | 102 | 47.16 | 6.31 | 4.54 | 103 | — | 3.41 |
| Tetramethylammonium trihydrogen di-maleate | 104–106 | 47.21 | 6.27 | 4.59 | 102 | 47.48 | 6.35 | 4.61 | 101 | 2.07 | 2.16 |
| Tetramethylammonium trihydrogen di-phthalate | 149–152 | 59.25 | 5.72 | 3.46 | 135 | 59.26 | 5.98 | 3.77 | 135 | — | 3.38 |
| Tetraethylammonium trihydrogen di-phthalate | 104–107 | 62.46 | 6.77 | 3.03 | 154 | 62.90 | 7.04 | 3.16 | 155 | — | 3.37 |
| Tri-n-propylammonium trihydrogen di-glutarate | 65–67 | — | — | 3.44 | 136 | — | — | 3.37 | 136 | 4.18 | 4.69 |
| Di-tert-butylammonium tetrahydrogen tri-fumarate | 191–193d | 48.58 | 6.93 | 5.66 | 124 | 48.49 | 6.98 | 5.71 | 125 | — | 3.58 |
| Di-tetraethylammonium tetrahydrogen tri-fumarate | 151–154 | 55.43 | 8.31 | 4.62 | 152 | 55.45 | 8.28 | 4.68 | 155 | — | 3.63 |

TABLE 1-continued

| Salt | mp, °C. | Calcd | | | | Found | | | | pH | |
| --- | --- | --- | --- | --- | --- | --- | --- | --- | --- | --- | --- |
| | | C | H | N | NE | C | H | N | NE | $H_2O$ | $H_2O$-glycol |
| Bis-(tri-n-propylammonium) tetrahydrogen tri-adipate | 50–51 | 59.64 | 10.01 | 3.86 | 181 | 59.80 | 9.99 | 3.91 | 182 | 4.45 | 4.97 |
| Di-N—ethylpiperidinium tetrahydrogen tri-succinate | 62–63 | 53.78 | 8.33 | 4.82 | 145 | 53.97 | 8.41 | 4.82 | 148 | 4.30 | 4.80 |

The salts were prepared by adding the amine with cooling to the acid suspended or dissolved in a moderate volume of solvent, commonly methanol or 2-propanol. The salts generally crystallized on cooling and adding ether or hexane. When crystallization did not occur, the mixture was taken to dryness at the water pump, and the crude products were crystallized from methanol, 2-propanol, or acetone, or these solvents combined with ether or hexane. When the base was a quaternary ammonium hydroxide, it was added to the acid in water or methanol. The following detailed procedures are illustrative.

An anomalous salt of the $RH_3Y_2$ type was prepared by adding 0.05 mole of tetramethylammonium hydroxide (46 ml of a 10% aqueous solution) to 0.1 mole fumaric acid. The mixture was warmed and enough methanol added to complete solution. The solution was taken to dryness with a water pump, and the crude product was crystallized from methanol-ether in a 72.3% yield. Its melting point was 191°–199° $C_d$, and recrystallization from methanol-ether raised the melting point to 199° $C_d$. Using an acid:base ratio of 3:2, the yield dropped to 68.7% and to 44.5% at a 1:1 ratio.

Another anomalous salt of the $RH_3Y_2$ type was prepared by adding 0.05 mole of tetraethylammonium hydroxide as a 10% solution in water to 0.1 mole phthalic acid. The solution was taken to dryness with a water pump, and the crude product was crystallized from 2-propanol-ether in a 93% yield. The melting point was 106°–107° C. and was unchanged by recrystallization from either 2-propanol-ether or acetonitrile.

A salt of the $R_2H_4Y_3$ type was prepared by adding 0.15 mole fumaric acid to 0.05 mole tetraethylammonium hydroxide as a 10% solution in water. Methanol was added, and the mixture was heated until solution was complete. The solution was taken to dryness with a water pump, and the crude product was recrystallized in 96% yield from methanol-ether. Its melting point was 151°–154° C. It can be recrystallized repeatedly from methanol-ether without changing the melting point, but recrystallization from 2-propanol converts the salt quantitatively to the normal salt, tetraethylammonium hydrogen fumarate, m.p. 245°–249° C.

What is claimed is:

1. An anomalous substituted-amine or quaternary ammonium salt of a dibasic acid wherein said salt is selected from the group consisting of salts containing two dibasic acid molecules per cation, $RH_3Y_2$, and salts containing three dibasic acid molecules per two cations, $R_2H_4Y_3$, wherein R is a quaternary ammonium or substituted-amine cation derived from the group consisting of tert-butylamine, tri-n-propylamine, N-ethylpiperidine, tetramethylammonium hydroxide and tetraethylammonium hydroxide, and $H_2Y$ is a dibasic acid molecule chosen from the group consisting of adipic, fumaric, glutaric, maleic, phthalic, and succinic acids.

2. A salt according to claim 1 wherein said salt is tetramethylammonium trihydrogen di-fumarate.

3. A salt according to claim 1 wherein said salt is tetramethylammonium trihydrogen di-maleate.

4. A salt according to claim 1 wherein said salt is tetramethylammonium trihydrogen di-phthalate.

5. A salt according to claim 1 wherein said salt is tetraethylammonium trihydrogen di-phthalate.

6. A salt according to claim 1 wherein said salt is tri-n-propylammonium trihydrogen di-gluterate.

7. A salt according to claim 1 wherein said salt is di-(tert-butylammonium) tetrahydrogen tri-fumarate.

8. A salt according to claim 1 wherein said salt is di-tetraethylammonium tetrahydrogen tri-fumarate.

9. A salt according to claim 1 wherein said salt is bis-(tri-n-propylammonium) tetrahydrogen tri-adipate.

10. A salt according to claim 1 wherein said salt is di-N-ethylpiperidinium tetrahydrogen tri-succinate.

* * * * *